United States Patent
Biedermann

(10) Patent No.: US 6,423,098 B1
(45) Date of Patent: Jul. 23, 2002

(54) LEG PROSTHESIS WITH AN ARTIFICIAL KNEE JOINT PROVIDED WITH AN ADJUSTMENT DEVICE

(75) Inventor: Lutz Biedermann, VS-Villingen (DE)

(73) Assignee: Biedermann Motech GmbH (DE)

( * ) Notice: Subject to any disclaimer, the term of this patent is extended or adjusted under 35 U.S.C. 154(b) by 0 days.

(21) Appl. No.: 09/367,198

(22) PCT Filed: Dec. 10, 1998

(86) PCT No.: PCT/EP98/08039
§ 371 (c)(1),
(2), (4) Date: Aug. 9, 1999

(87) PCT Pub. No.: WO99/29272
PCT Pub. Date: Jun. 17, 1999

(30) Foreign Application Priority Data

Dec. 10, 1997 (DE) .......................................... 197 54 690

(51) Int. Cl.[7] .............................. A61F 2/64; A61F 2/70; A61F 2/74
(52) U.S. Cl. .............................. 623/24; 623/26; 623/44
(58) Field of Search .............................. 623/24–27, 39, 623/43–46, 57, 58

(56) References Cited

U.S. PATENT DOCUMENTS

| | | | |
|---|---|---|---|
| 5,443,524 A | 8/1995 | Sawamura et al. ........... 623/24 |
| 5,571,205 A | 11/1996 | James .......................... 623/24 |
| 5,645,752 A | * 7/1997 | Weiss et al. ............. 252/62.54 |
| 5,752,891 A | * 5/1998 | Meckstroth et al. ........ 474/110 |

FOREIGN PATENT DOCUMENTS

| | | |
|---|---|---|
| DE | 43 05213 A1 | 8/1993 |
| DE | 43 18901 A1 | 1/1994 |
| DE | 195 21 464 A1 | 3/1997 |
| EP | 0 503 775 A1 | 9/1992 |
| EP | 0 628 296 A | 12/1994 |
| FR | 2 623 086 A | 5/1989 |
| GB | 1 191 633 | 5/1970 |
| GB | 2 244 006 A | 11/1991 |
| WO | WO 96/41599 | 12/1996 |

* cited by examiner

Primary Examiner—David H. Willse
(74) Attorney, Agent, or Firm—George W. Neuner, Esq.; Edwards & Angell LLP

(57) ABSTRACT

A leg prosthesis having an artificial knee joint with swing phase control and recoil break comprises a damping member acting upon the knee joint, detectors for detecting force, knee angle and acceleration and a control unit for controlling the dampening degree of the damping member on the basis of the detected values. The damping characteristics of the damping member are varied in dependence on control signals produced by the control unit on the basis of a viscosity change of the magneto-rheological liquid.

9 Claims, 1 Drawing Sheet

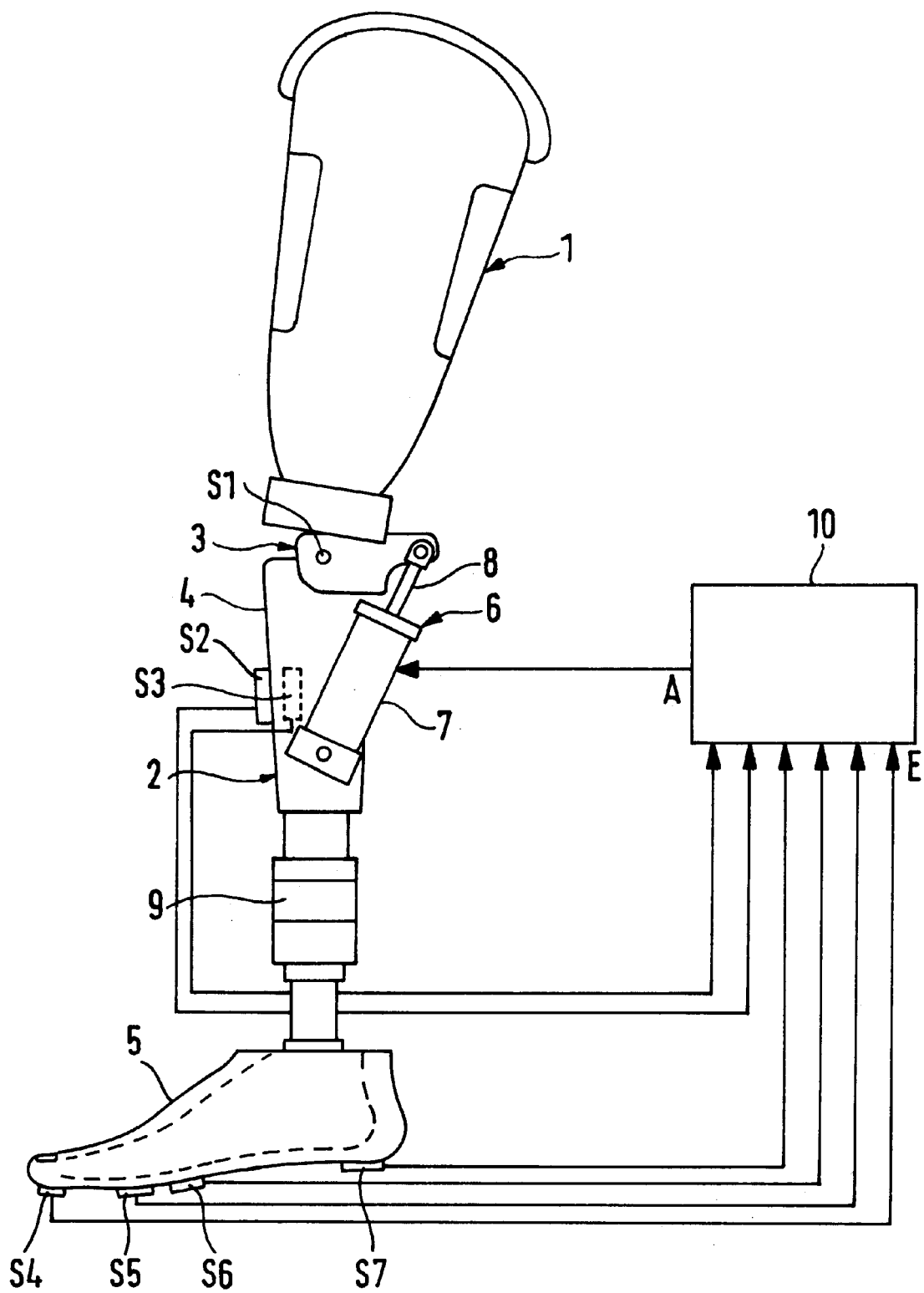

LEG PROSTHESIS WITH AN ARTIFICIAL KNEE JOINT PROVIDED WITH AN ADJUSTMENT DEVICE

The invention relates to a leg prosthesis comprising an artificial knee joint having swing phase control and recoil brake wherein a control member provided at the knee joint controls the knee joint depending on control signals based on a viscosity change of a magneto-rheological liquid.

When walking with a prosthesis the thigh member is moved forward by the residual limb. The leg member may, owing to its mass inertia, bend back very far if the damping is not properly adjusted. The wearer of the prosthesis then has to wait until the prosthesis moves again in forward direction before putting the foot on the ground. This results in an unharmonious walking appearance, an unfavourable time characteristic and therefore poor wearing properties.

It is known to provide leg prostheses comprising an artificial knee joint with a damping member formed as a pneumatic or hydraulic cylinder for swing phase control and as a so-called recoil brake. The leg prosthesis is adapted to the wearer by means of a stationary walking pattern analysis system. The wearer of the prosthesis must do a test run, for example on a walking band, and the walking pattern is then subjectively evaluated by an orthopedic technician.

Taking also the subjective sensations of the wearer of the prosthesis into account, the various components of the prosthesis are then adapted and adjusted. The result of this adjustment is often inaccurate because it is based on subjective criteria. Further, later changes such as weight changes, temperature changes or changes of the ground conditions are not taken into consideration.

Moreover, the known damping members for artificial knee joints are disadvantageous in that they are unable to react in a sufficiently fast manner to an abrupt change of the walking dynamics.

It is the object of the invention to provide a leg prosthesis comprising an artificial knee joint with a swing phase control and a recoil brake, the leg prosthesis ensuring an always optimum operation which is adapted to the wearer as well as fast reaction to abrupt changes of the walking dynamics.

This object is achieved by a control based on a viscosity change of a magneto-rheological liquid and an automatic control producing control signals on the basis of detected values to automatically regulate the knee joint functions during the operation of the prothesis.

Further features and advantages of the invention will be apparent from the description of an embodiment with reference to the FIGURE.

The FIGURE shows, in schematic representation, a leg prosthesis comprising an artificial knee joint with a swing phase control and a recoil brake and a corresponding control or regulation, respectively.

In conventional manner the prosthesis comprises a thigh member 1 and a leg member 2 and a knee joint 3 joining both members.

The leg member 2 comprises a shin part 4 having a lower leg tube 9 and a foot member 5 attached thereto. The foot member 5 comprises a leaf spring which is not shown in the FIGURE for allowing resilient steps. The thigh member 1 is formed for connection with the residual limb.

The knee joint 3 comprises a damping member in form of a hydraulic piston-cylinder device 6. The piston 7 of the piston-cylinder device 6 is connected to the shin part 4 and the piston rod 8 of the piston-cylinder device 6 is connected with the knee joint 3. The cylinder of the piston-cylinder device is filled with a magneto-rheological liquid (MR fluid) having the characteristics of changing its viscosity within about 3 to 5 milliseconds when subjected to a magnetic field. The magneto-rheological liquid consists of a suspension of magnetizable particles having a size on the order of micrometers in oil. Under normal circumstances the consistence of a magneto-rheological liquid is similar to that of engine oil. When subjected to a magnetic field the viscosity abruptly increases whereby the change is proportional to the intensity of the magnetic field.

The piston 8 or the cylinder 7 of the piston-cylinder device 6 further comprises a solenoid which can be controlled by external signals and generates the magnetic field affecting the magneto-rheological liquid.

The leg prosthesis further comprises a number of sensors for detecting motion and force. A knee angle detector for detecting the knee angle is provided in the knee joint 3. Acceleration detectors are provided at the shin part 4. A head-on acceleration detector S2 serves for measuring the acceleration in walking direction, a lateral acceleration detector S3 serves for measuring the acceleration perpendicular to the walking direction. The acceleration detectors may be conventional acceleration detectors which are for example used in vehicle technology. Further, force detectors S4 to S7 are provided in the region of the foot sole. The force detector S4 is located in the region of the toes, the force detectors S5 and S6 are located in the region of the ball of the foot and the force detector S7 is located in the heel region. The detectors may be conventional force detectors, for example based on a compression spring. Alternatively, force sensors located within the lower leg tube 9 may be used.

The signal outputs of the detectors S1 to S7 are connected to one or several inputs E of a control or regulation unit 10.

The control unit comprises a CPU and a data memory. A program having a algorithm for processing the incoming signals of the sensors and for producing one or several output signals is provided in the data memory. A signal output A of the control unit 10 is connected with the piston-cylinder device 6 and especially with the solenoid provided within the piston.

In operation the control of the leg prosthesis works as follows.

The measurement data of the detectors S1 and S7 are transmitted to the control unit 10. Based on the measurement data control unit 10 produces control signals for the piston-cylinder device and transmits them to this device. Based on the control signals the solenoid produces a defined magnetic field which causes a determined viscosity change of the magneto-rheological liquid in the cylinder 7. By changing the viscosity the depth of immersion of the piston 9 into the cylinder 7 and therefore the damping effect can be correspondingly controlled. The damping change thereby occurs within a period of about 3 to 5 milliseconds. This is particularly advantageous when using the damping as recoil brake. If the wearer of the leg prosthesis stumbles, the leg member can be prevented in good time from folding up by the damping effect which immediately builds up.

The control unit, the detectors and the damping member are interconnected in a control circuit, i.e. the damping effect is adjusted during walking. This is advantageous, compared to a conventional prosthesis control, in that the prosthesis functions are adjusted in direct dependence on the natural walking pattern of the wearer of the prosthesis.

Modified embodiments are possible. More or less than the above-described detectors may be provided.

In place of the piston-cylinder device having a cylinder with an axially displaceable piston therein a piston-cylinder device comprising a rotary piston may be used. The rotary piston can be provided with vanes having a defined resistance within the cylinder dependent on the viscosity of the magneto-rheological liquid. In this case, the piston rod is connected to a rotary shaft of the knee joint.

What is claimed is:

1. A leg prosthesis having an artificial knee joint with swing phase control and recoil brake, said prosthesis comprising:

means for producing control signals for controlling said knee joint; and a control member controlling said knee joint on the basis of said control signals;

said control member comprising a damping member in the form of a piston cylinder device having a piston and a cylinder filled with a magneto-rheological liquid and means for changing the viscosity of said magneto-rheological liquid within the cylinder on the basis of said control signals, wherein a damping effect is provided by the piston in the cylinder.

2. The leg prosthesis of claim 1, said means for producing control signals comprising a detector provided at said leg prosthesis, said detector including (A) a detector selected from the group consisting of (1) a force detector, (2) a knee angle detector or (3) an acceleration detector having a signal output, and (B) a control unit connected to said signal output of said detector for producing said control signals on the basis of the values of force, knee angle or acceleration detected by said detector.

3. The leg prosthesis of claim 2 comprising a detector selected from the group consisting of:

(1) a detector provided at the knee joint for detecting the knee angle, (2) a detector provided in the region of a shin for detecting a lateral or forward acceleration, or (3) a force detector provided at the sole.

4. The leg prosthesis of claim 2, further comprising a regulating unit for automatic regulation of the knee joint functions during the walking on the basis of the actually detected values of force, acceleration or knee angle, said regulation unit comprising said knee joint, said control unit and said control member.

5. The leg prosthesis of claim 2, wherein said control unit is mounted to said leg prosthesis and fixedly connected to said control member.

6. The leg prosthesis of claim 1, wherein said means for changing the viscosity of said magneto-rheological liquid is a solenoid, and said control member controls said solenoid for varying the magnetic field produced by said solenoid on the basis of said control signals.

7. A leg prosthesis according to claim 1, said leg prosthesis further comprising:

at least one detector provided at said prosthesis for detection of force, knee angle or acceleration, said detector having a signal output; and a control unit connected to said signal output for producing control signals on the basis of the values detected by said detector;

wherein said control member is provided at said knee joint for automatically controlling said knee joint on the basis of said control signals during operation of said prosthesis.

8. The leg prosthesis of claim 1, wherein said piston-cylinder device comprises an axially displaceable piston or a rotary piston.

9. A leg prosthesis having an artificial knee joint with swing phase control and recoil brake, said prosthesis comprising:

means for producing control signals for controlling said knee joint;

at least one detector provided at said prosthesis for detection of force, knee angle or acceleration, said detector having a signal output;

a control unit connected to said signal output for producing control signals on the basis of the values detected by said detector; and a control member provided at said knee joint for automatically controlling said knee joint on the basis of said control signals during operation of said prosthesis;

said control member comprising a piston and a cylinder filled with a magneto-rheological liquid and means for changing the viscosity of said magneto-rheological liquid on the basis of said control signals, wherein said magneto-rheological liquid provides resistance within the cylinder, thereby providing a damping effect on the piston.

* * * * *